United States Patent
Doyon et al.

(10) Patent No.: US 8,756,720 B2
(45) Date of Patent: Jun. 24, 2014

(54) MULTIPLE LENS GEOMETRIES FOR SAFETY GLASSES

(75) Inventors: Jean-Christophe Doyon, Terrebonne (CA); Marc Lamontagne, Repentigny (CA); Michel Landry, Mascouche (CA); Paul Isabelle, St-Agustin-de-Desmaures (CA)

(73) Assignee: Honeywell International Inc, Morristown, NJ (US)

(*) Notice: Subject to any disclaimer, the term of this patent is extended or adjusted under 35 U.S.C. 154(b) by 324 days.

(21) Appl. No.: 12/773,571

(22) Filed: May 4, 2010

(65) Prior Publication Data

US 2011/0271431 A1 Nov. 10, 2011

(51) Int. Cl.
*A61F 9/02* (2006.01)

(52) U.S. Cl.
USPC .................................. 2/439; 351/47

(58) Field of Classification Search
CPC ............ G02C 11/08; G02C 1/04; G02C 5/02; G02C 7/10; G02C 5/124; G02C 5/2263; A61F 9/25
USPC ............ 2/439, 446, 447; 351/44, 47, 116, 55, 351/136, 137, 138, 120, 85, 86
See application file for complete search history.

(56) References Cited

U.S. PATENT DOCUMENTS

| 2,444,498 | A | * | 7/1948 | Cochran | 351/60 |
|---|---|---|---|---|---|
| 2,685,819 | A | * | 8/1954 | Page | 351/55 |
| 3,667,834 | A | * | 6/1972 | Davison | 351/118 |
| 3,846,018 | A | * | 11/1974 | Gerson | 351/120 |
| 4,113,365 | A | | 9/1978 | Koketsu | |
| 4,240,718 | A | | 12/1980 | Wichers | |
| 4,405,214 | A | | 9/1983 | Bolle | |
| 4,500,179 | A | | 2/1985 | Schonhut | |
| 4,544,245 | A | | 10/1985 | Stansbury, Jr. | |
| 4,556,300 | A | | 12/1985 | Dietrich | |
| 4,670,915 | A | * | 6/1987 | Evans | 2/450 |
| 4,674,851 | A | * | 6/1987 | Jannard | 351/47 |
| 4,704,015 | A | | 11/1987 | Grendol et al. | |
| 4,730,915 | A | | 3/1988 | Jannard | |

(Continued)

FOREIGN PATENT DOCUMENTS

| EP | 1 376 200 A1 | 2/2004 |
|---|---|---|
| FR | 2 652 167 | 3/1991 |
| WO | WO 2004/083941 A1 | 9/2004 |

OTHER PUBLICATIONS

European Search Report corresponding to Application No. EP 11 16 4360, dated Aug. 10, 2011.

(Continued)

*Primary Examiner* — Khoa Huynh
*Assistant Examiner* — Anna Kinsaul
(74) *Attorney, Agent, or Firm* — Barlow, Josephs & Holmes, Ltd.

(57) ABSTRACT

A family of eye protectors for use with a variety of shapes and sizes of heads includes a plurality of different lenses with each lens having a selected curvature and selected height and profile parameters; and a manually adjustable nose engaging element carried on each lens. The nose engaging element can include a substantially U-shaped frame which has first and second deflectable, spaced apart members joined by a third member. A plurality of identical mounting elements can be proved wherein each mounting element holds one of said plurality of different lenses.

11 Claims, 7 Drawing Sheets

(56) References Cited

U.S. PATENT DOCUMENTS

| | | | |
|---|---|---|---|
| 4,780,928 A | | 11/1988 | De Lorenzo Poz |
| 4,806,009 A | | 2/1989 | Sordillo et al. |
| 4,824,233 A | * | 4/1989 | Jannard .................. 351/47 |
| 4,890,356 A | | 1/1990 | Czech et al. |
| 4,955,708 A | | 9/1990 | Kahaney |
| 5,009,495 A | | 4/1991 | Williams |
| 5,032,017 A | * | 7/1991 | Bolle et al. .................. 351/116 |
| 5,133,595 A | | 7/1992 | Gutbrod et al. |
| 5,229,796 A | | 7/1993 | Nitta |
| 5,315,328 A | | 5/1994 | Hofmair et al. |
| D350,759 S | | 9/1994 | Lanna et al. |
| 5,347,325 A | | 9/1994 | Lei |
| 5,412,438 A | | 5/1995 | Bolle' |
| 5,426,473 A | | 6/1995 | Riehm |
| 5,457,503 A | | 10/1995 | Chen |
| 5,467,148 A | * | 11/1995 | Conway .................. 351/85 |
| 5,483,303 A | | 1/1996 | Hirschman |
| 5,526,070 A | | 6/1996 | Simioni |
| 5,532,767 A | | 7/1996 | Pleune et al. |
| 5,541,674 A | | 7/1996 | Jannard |
| 5,565,937 A | | 10/1996 | Lee |
| 5,596,789 A | | 1/1997 | Simioni |
| 5,614,964 A | | 3/1997 | Garneau |
| 5,646,707 A | | 7/1997 | Arnette |
| D384,092 S | | 9/1997 | Hall et al. |
| 5,689,835 A | | 11/1997 | Chao |
| 5,703,669 A | * | 12/1997 | Park .................. 351/86 |
| 5,737,055 A | | 4/1998 | Dittmeier |
| 5,757,457 A | * | 5/1998 | Conway .................. 351/138 |
| 5,768,716 A | * | 6/1998 | Porsche .................. 2/454 |
| 5,771,087 A | | 6/1998 | Martin et al. |
| 5,790,230 A | | 8/1998 | Sved |
| 5,796,461 A | | 8/1998 | Stepan |
| 5,812,234 A | | 9/1998 | Carswell |
| D411,211 S | | 6/1999 | Higuchi et al. |
| 5,946,072 A | | 8/1999 | Canavan |
| 5,956,115 A | | 9/1999 | Bolle' |
| 5,969,787 A | | 10/1999 | Hall et al. |
| 5,980,038 A | | 11/1999 | Chen |
| D419,579 S | | 1/2000 | Hall et al. |
| D420,027 S | | 2/2000 | Hall et al. |
| D420,034 S | | 2/2000 | Actis-Davis et al. |
| 6,019,467 A | | 2/2000 | Kawamoto |
| 6,036,312 A | | 3/2000 | Stepan |
| D423,033 S | | 4/2000 | Hall et al. |
| 6,050,684 A | | 4/2000 | Mage |
| D424,080 S | | 5/2000 | Hall et al. |
| RE36,762 E | | 7/2000 | Canavan et al. |
| 6,086,200 A | | 7/2000 | Wang-Lee |
| 6,250,756 B1 | | 6/2001 | Jannard et al. |
| 6,257,719 B1 | | 7/2001 | Pavlak |
| 6,280,030 B1 | * | 8/2001 | Chen .................. 351/86 |
| 6,364,480 B1 | | 4/2002 | Chen |
| 6,367,927 B2 | * | 4/2002 | Yang .................. 351/103 |
| 6,386,705 B1 | | 5/2002 | Chen |
| 6,454,406 B1 | | 9/2002 | Guo |
| 6,464,353 B1 | | 10/2002 | Spindelbalker |
| 6,464,354 B1 | | 10/2002 | Chen et al. |
| 6,513,925 B1 | | 2/2003 | Bonacci |
| 6,520,636 B2 | | 2/2003 | Saitoh et al. |
| 6,575,569 B1 | | 6/2003 | Castellano |
| 6,575,570 B2 | | 6/2003 | Mauri |
| 6,582,074 B1 | | 6/2003 | Chen |
| D483,791 S | | 12/2003 | Thixton et al. |
| 6,666,554 B2 | | 12/2003 | Mulvey |
| 6,692,124 B2 | | 2/2004 | Katz et al. |
| D492,340 S | | 6/2004 | Cyr |
| 6,793,336 B2 | | 9/2004 | Min |
| 6,817,709 B2 | | 11/2004 | Min |
| 6,908,193 B2 | | 6/2005 | Cyr |
| 6,939,004 B1 | | 9/2005 | Chen |
| D513,025 S | | 12/2005 | Canavan |
| 6,976,756 B1 | | 12/2005 | Chen |
| D513,761 S | | 1/2006 | Yee et al. |
| 6,991,333 B2 | | 1/2006 | Van Atta et al. |
| 6,994,434 B2 | | 2/2006 | Blanchette et al. |
| 7,018,036 B2 | | 3/2006 | Yamamoto |
| 7,431,451 B1 | * | 10/2008 | Lin .................. 351/138 |
| 7,543,932 B1 | | 6/2009 | Isabelle et al. |
| 2006/0007389 A1 | * | 1/2006 | Fusi et al. .................. 351/116 |
| 2007/0263168 A1 | | 11/2007 | Cohen et al. |
| 2009/0219481 A1 | | 9/2009 | Lamontagne |

OTHER PUBLICATIONS

English translation of abstract of FR 2 652 167 Published: Mar. 22, 1991.

* cited by examiner

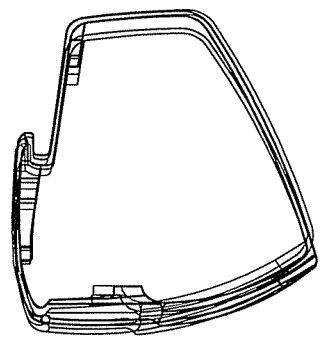
FIG. 1D SIDE
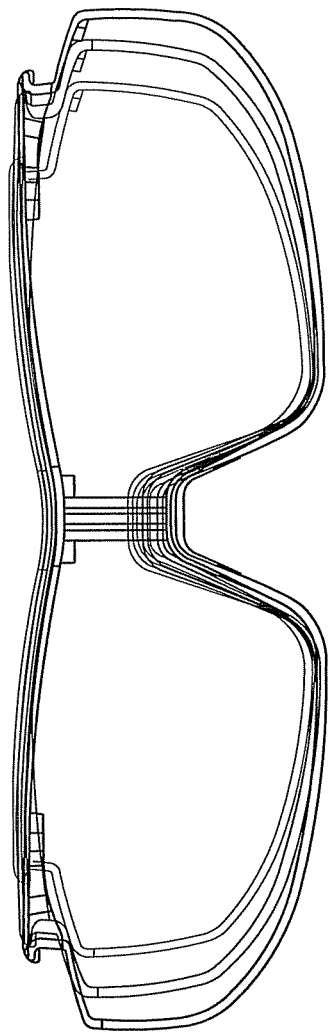
FIG. 1B FRONT
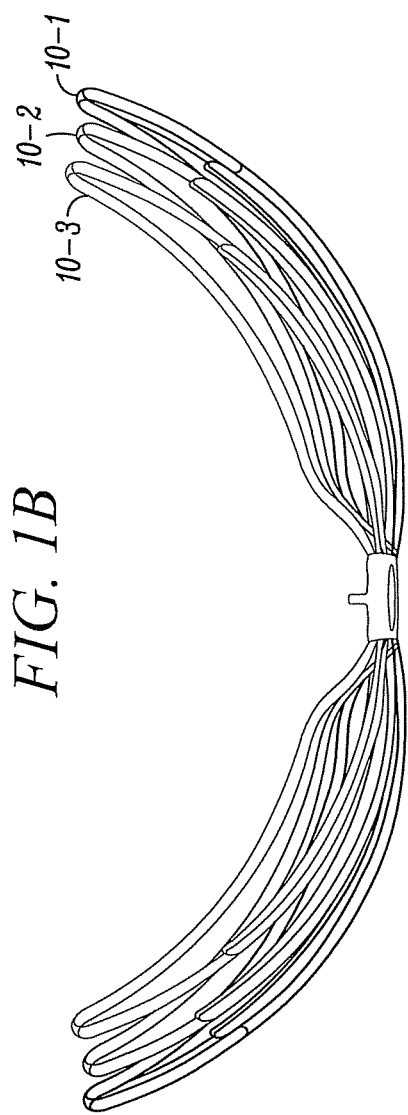
FIG. 1C TOP

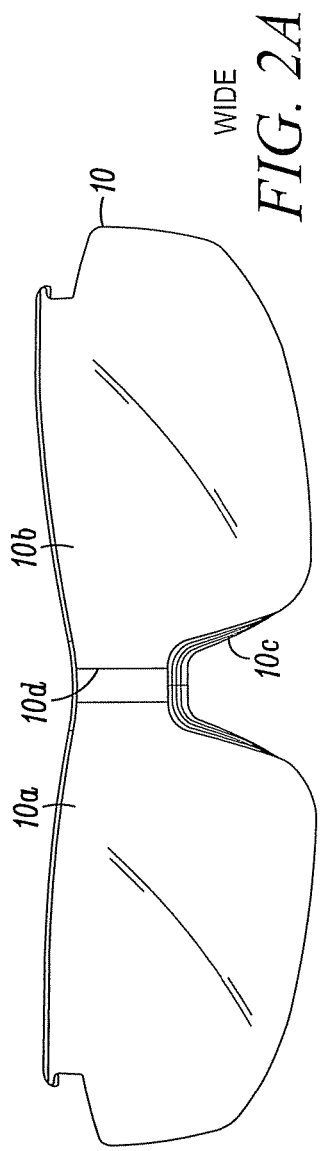
FIG. 2A WIDE
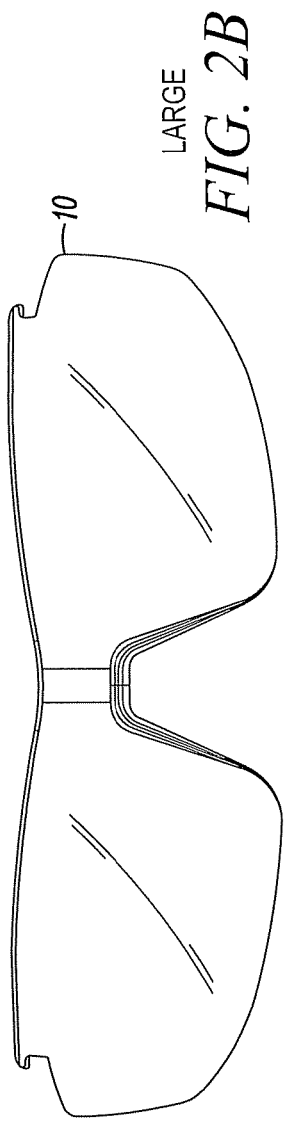
FIG. 2B LARGE
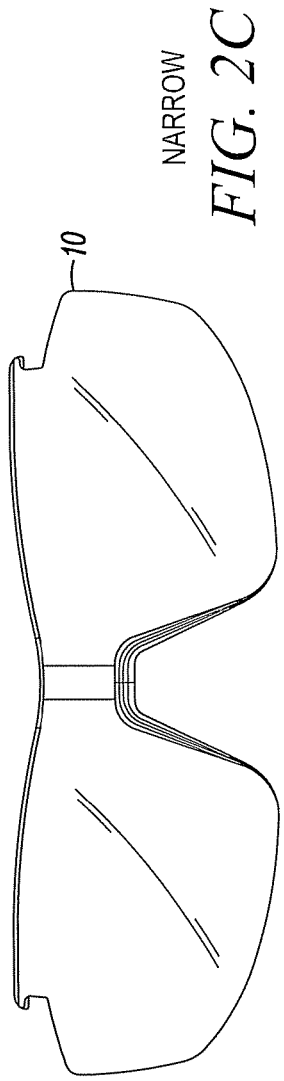
FIG. 2C NARROW
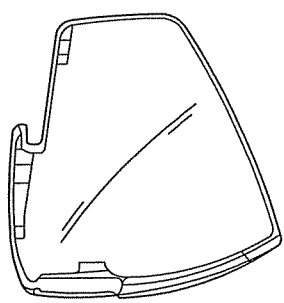
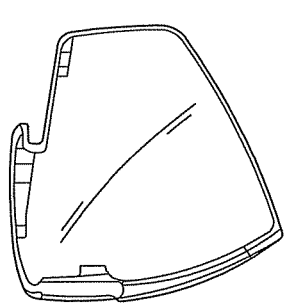
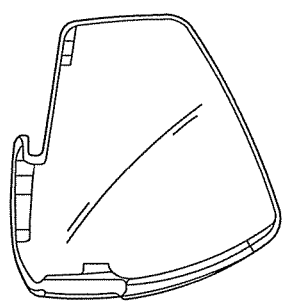

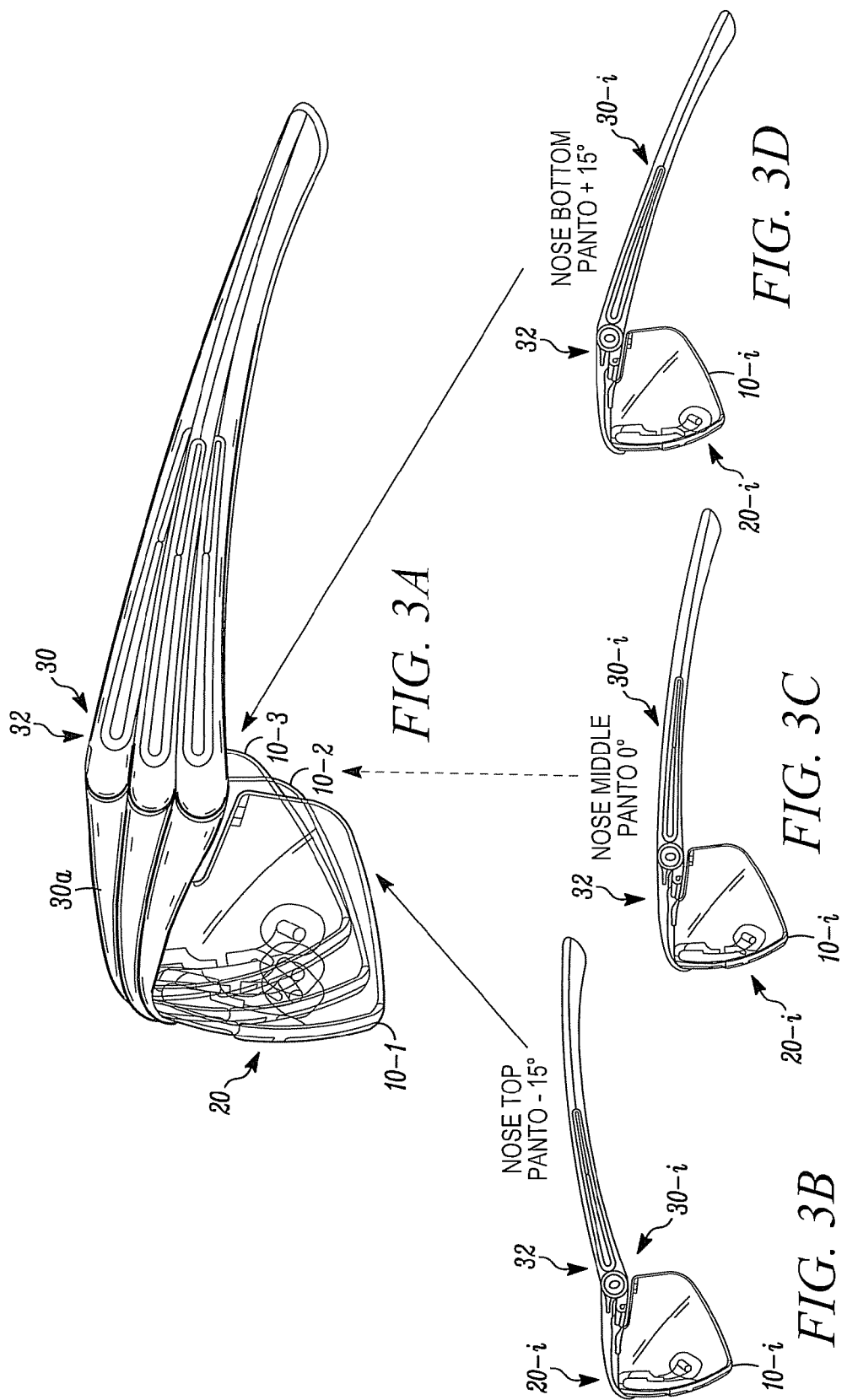

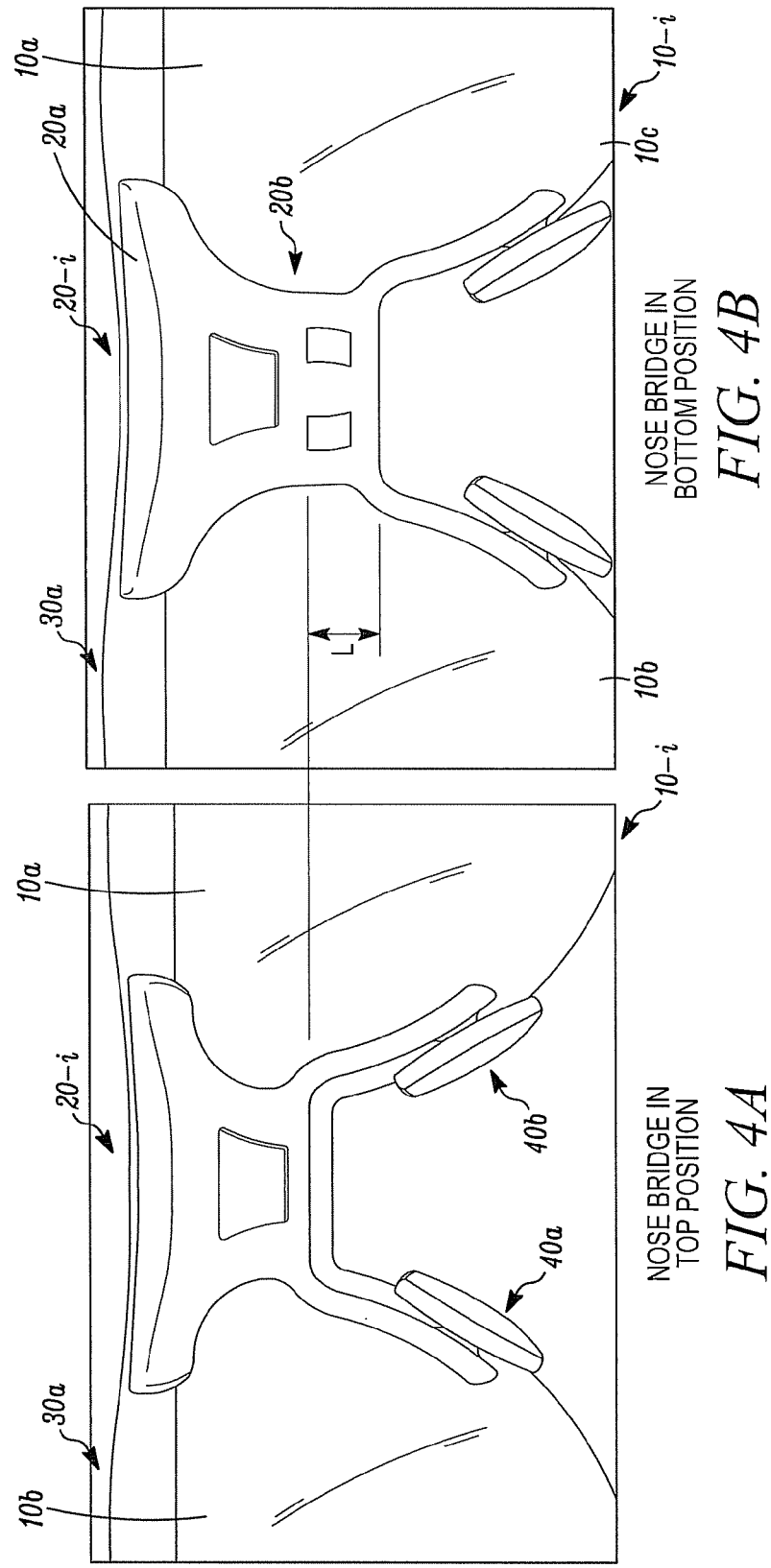

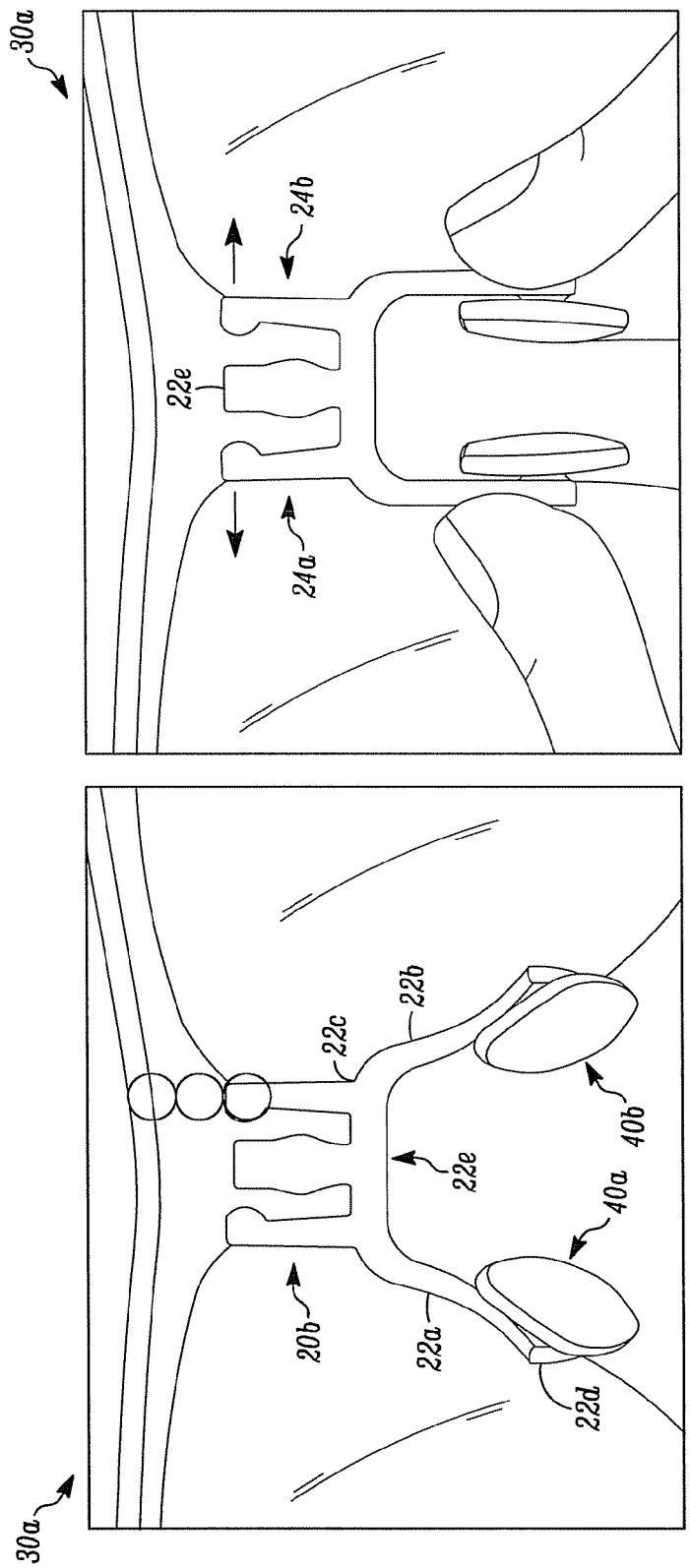

MULTIPLE LENS GEOMETRIES FOR SAFETY GLASSES

FIELD

The invention pertains to safety glasses of various geometries usable with different sizes and shapes of human heads. More particularly, the invention pertains to modular structures from which different geometries of glasses can be implemented using common elements.

BACKGROUND

Various sizes and types of safety glasses, or sun glasses are known. The known types attempt to address different sizes and shapes of human heads.

Some of the known products include multiple sets of lenses and other adjustments. Some of the products include adjustable nose pads and temples.

There is an on-going need to provide various sizes of safety glasses which are comfortable and fit well, but at the same time provide a good level of protection for the users.

BRIEF DESCRIPTION OF THE DRAWINGS

FIGS. 1A-1D illustrate different views of a family of unitary lenses in accordance with the invention;

FIGS. 2A-2C illustrate additional details of the members of the family of unitary lenses of FIGS. 1A-1D;

FIGS. 3A-3D illustrate aspects of a family of safety glasses in accordance with the invention;

FIGS. 4A, 4B illustrate aspects of an adjustable nose bridge usable with the safety glasses of FIGS. 3A-3D;

FIGS. 5A, 5B illustrate adjusting the nose bridge illustrated in FIGS. 4A, 4B; and;

DETAILED DESCRIPTION

Figure 1A:
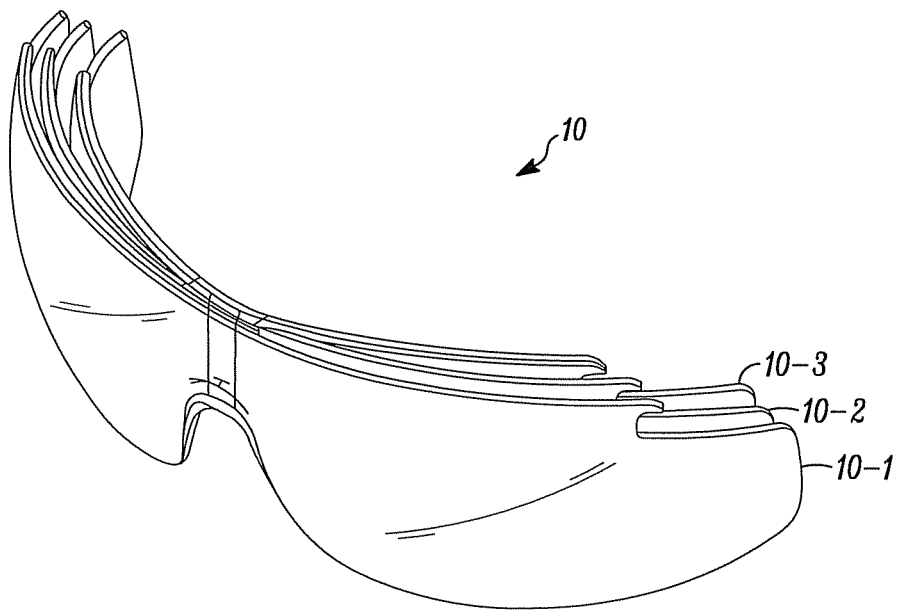

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In one aspect of the invention, a family of lenses is provided. In this regard, the lenses can have a common curvature along with similar height parameters and profiles.

In embodiments of the invention, differentiation between the members of the family of lenses can be achieved by changing the base curvature of the lenses, changing the pupillary distance and by varying the pantoscopic angle. Representative lens sizes can be categorized as large, wide and narrow. Each lens can be formed with a different base. Various degrees of nose cut can be provided on different family members.

In other embodiments of the invention, the nose pads can be adjusted. Additionally, the temples can be adjustable. In yet another aspect of the invention, the lenses can be shaped with a curve 8, 9, or 10 base all without limitation. A common set of temples can be used for the various members of the family of lenses.

The adjustment features make it possible to adjust the respective lens so that the lens' optical center aligns with the center of the pupil of the user's eyes. This advantageously eliminates vertical prism imbalance to reduce eye strain and fatigue, maximizes the resolving power of the lens, reduces haze for a clearer field of view and reduces perception of chromatic and spherical aberration.

In yet another aspect of the invention, safety glasses in accordance with the invention can be adjusted such that the lens does not come into contact with the wearer's skin. This reduces the risk of lens fogging. Further, gaps can be left between the respective lens and the face of the wearer to protect the wearer's eyes from flying objects and particles.

In one embodiment, of the invention, three different lens geometries can be provided identifiable as wide, large, and narrow, depending on the geometry of the expected wearer's face. Differences in respective members of the families relate to optical and geometrical parameters such as pantoscopic angle and papillary distance.

A user manipulatable, vertically adjustable nose portion makes it possible for a user to adjust the lens without any need for a tool. Pivotable, and deformable nose pads can be provided to increase user comfort. Finally, detents can be provided limiting adjustments to a plurality of vertical positions to increase ease and simplicity of adjustment.

A first part of a nose locking element can be carried on the frame at the center of the lens. A three sided bridge, with two spaced apart arms, joined by a center section can carry nose pads. The bridge can be locked to the locking element in each of a plurality of generally vertical positions.

The center section can carry locking arms, which engage the first part of the nose locking element on the frame. Deflecting the nose pads toward one another releases the arms to adjust the bridge. Spreading the nose pads apart, for example as when wearing the glasses, further locks the bridge to the first part.

In one disclosed embodiment, the nose pads can be formed as a co-injected, dual material, member. Such nose pads can provide ball joint-like movement without requiring assembly.

With respect to the figures, FIGS. 1A-1D illustrate members 10-1, -2, -3 of an exemplary family of lenses 10. The members of the family 10 are shaped with a common curve 9 base. They have the same height and profile shape except for the narrow, lens 10-3 which has longer side coverage and the wide lens 10-1 which has a shorter nose cut. FIGS. 2A, B, and C illustrate additional details of the shapes of each of the lenses. The lenses 10-1, -2, -3 can be formed with different bases 10$i$ as well as different height and profile shapes as desired.

FIG. 3A illustrates a family 30 of safety glasses built around the family of lenses 10. Each member of the family, such as 30-$i$ includes an adjustable nose element, indicated generally at 20. The adjustable nose element 20 also carries a pair of elastomeric nose contact pads.

Pivotably attached ear pieces, indicated generally at 32 provide an adjustable pantoscopic angle for the user, illustrated in FIGS. 3B, 3C and 3D. The adjustable nose elements 20 provide vertical adjustment so that the user, or, wearer of the glasses can center the lenses with his/her eyes while the pivotable ear pieces 32 provide the angular adjustment.

As illustrated in FIGS. 4A, 4B the safety glass can be considered frameless. The respective ear piece 32 can be attached directly to the lens or can be a separate part that will snap onto the lens and hold the temple arm. In another embodiment, the respective lens, such as 10-1 can carry a mounting element, such as 30$a$ to which the respective ear piece 32 can be attached. The adjustable nose element, such as 20-$i$ includes a cover 20$a$ and a vertically slidable adjustment structure 20$b$.

The structure 20b, as illustrated in FIGS. 5A, 5B, includes a U-shaped portion with arms 22a, b joined by a center section 22c. A free end, such as 22d, of each of the arms 22a, b carries a respective nose pad 40a, b. An extension 22e from the central section 22c slides in the slot 10d of the respective lens, such as 10-i, s the structure 20b is adjusted vertically L relative to the lens 10-1.

Manually squeezing the nose pads 40a,b toward each other as illustrated in FIG. 5B, releases the member 20-i from the mounting portion 30a to move vertically L as desired. Detents can be provided in the mounting portion 30a into which ends of locking arms 24a,b can move to lock the nose bridge 20-i into a selected location.

When the safety glasses are in use and nose pads 40a,b are in contact with the user's nose, the forces on the pads from the user's nose tend to spread them apart thus forcing arms 24a,b toward one another thereby locking the nose bridge 20b firmly in place relative to member 30a.

Figure 6A:
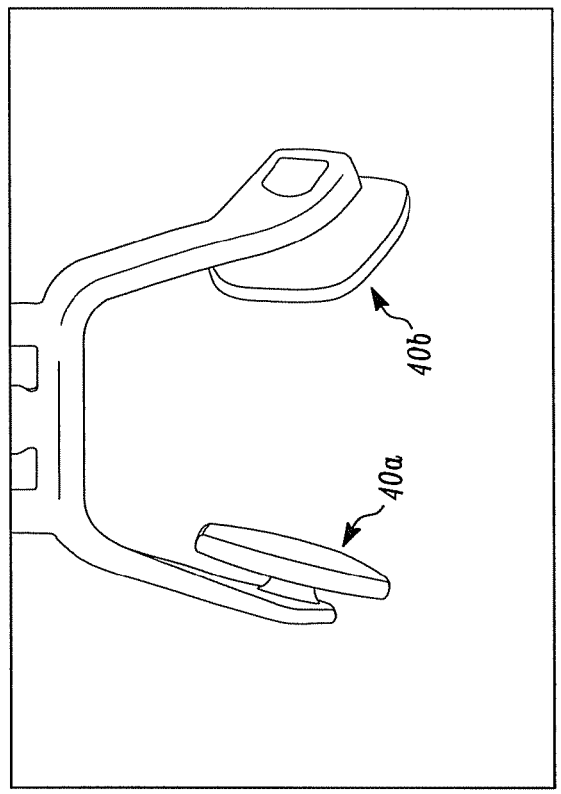
FIGS. 6A, 6B illustrate aspects of nose pads usable with the nose bridge of FIGS. 4A, 4B.
Figure 6B:
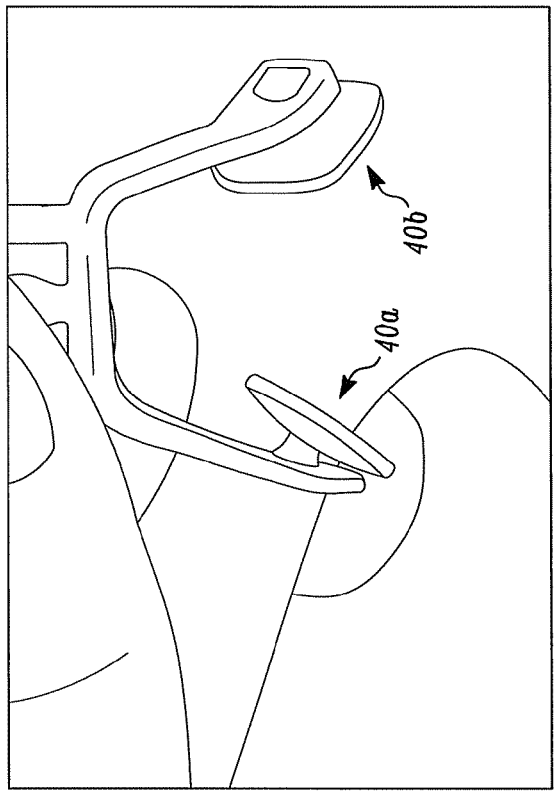

FIGS. 6A, 6B illustrates aspects of the nose pads 40a,b. Nose pads 40a,b can be formed of two elastomeric materials co-injected on the nose bridge 20b. This fabrication recreates ball joint-type movement very cost effectively. A further advantage is that no assembly is required.

In summary, a family of eye protectors can be based on a plurality of lenses. Each of the lenses has a different, anatomically based, shape with a common curvature and two spaced apart transparent optical elements 10a and 10b with a nose receiving region 10c therebetween.

First and second pivotable ear pieces can be coupled to respective first and second ends of a respective lens, with each ear piece adjacent to a respective optical element. The ear pieces provide an accurate adjustment, pantoscopic angle adjustment, for the eye protectors.

An adjustable, vertically movable, nose bridge is carried between the optical elements of a lens. Ends of the nose bridge carry soft, deformable nose pads.

The ends can be deflected toward one another to release the bridge from the lens for vertical movement therebetween. When the ends are released, they move apart and lock the bridge to the lens. In addition, when being worn, the ends are continually pushed apart thereby maintaining the relative position of the nose bridge relative to the lens.

A slot can be provided on the lens so the nose bridge can move freely to adjust the position of the lens relative to the user's eyes. The nose pads can be formed of two different, co-extruded elastomeric materials.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A family of eye protectors comprising:
a plurality of different unitary lenses with each lens having a common curvature and a different profile parameter;
a set of temples where the temples are at least one of rotatably adjustable relative to the lens, or, slidably adjustable relative to the lens;
each lens having a different size nose securing region; and
said family having one manually adjustable nose engaging element that can be carried on each of said plurality of different unitary lenses where each lens defines an adjustable nose element receiving slot;
wherein the adjustable nose engaging element includes a slidable lens engagement member which lockingly engages the respective lens at only a plurality of spaced apart locations;
wherein the eye protectors are frameless and
wherein the nose engaging element includes two separate, double molded nose contacting pads formed of two different elastomeric materials co-injected on a nose bridge producing pivotable ball joint-type movement.

2. A family as in claim 1 where the nose engaging element includes a substantially U-shaped frame which has first and second deflectable, spaced apart members joined by a third member.

3. A family as in claim 2 where the nose element includes a slidable lens engagement member.

4. A family as in claim 2 which includes one mounting element or a plurality of identical mounting elements wherein each mounting element holds one of said plurality of different unitary lenses.

5. A family as in claim 2 where each lens has a common curvature and defines a centrally located nose indentation.

6. A family as in claim 5 where the nose element is slidably receivable adjacent to the nose indentation.

7. A family as in claim 6 where the nose element includes a slidable lens engagement member and where the member slides, at least in part, in the slot.

8. A family as in claim 1 where the nose element moves generally perpendicularly toward and away from the lens.

9. Safety glasses comprising:
a plurality of different sized unitary lenses, the lenses have a common curvature, each lens has a height and a length parameter which are consistent with a user face shape selected from a class that includes a wide face, a narrow face and a large face;
a set of temples where the temples are at least one of rotatably adjustable relative to the lens, or, slidably adjustable relative to the lens
one manually adjustable nose engaging element that can be carried on each of said plurality of different sized unitary lenses, and
where each lens defines a manually adjustable nose engaging element receiving slot;
wherein the manually adjustable nose engaging element lockingly engages the respective lens at only a plurality of spaced apart locations;
wherein each lens has a different size nose securing region;
wherein the adjustable nose element includes a slidable lens engagement member;
wherein the safety glasses are frameless and
wherein the nose engaging element includes two separate, double molded nose contacting pads formed of two different elastomeric materials co-injected on a nose bridge producing pivotable ball joint-type movement.

10. Safety glasses as in claim 9 wherein said manually adjustable nose engaging element has at least one locking member that defines a plurality of nose engaging element locking locations spaced part from one another.

11. Safety glasses as in claim 10 with portions of the nose engaging element deflectable toward one another to unlock the nose engaging element for movement between locations.

* * * * *